(12) United States Patent
Khine et al.

(10) Patent No.: US 11,035,765 B2
(45) Date of Patent: Jun. 15, 2021

(54) DETECTION OF LOW CONCENTRATION BIOLOGICAL AGENTS

(71) Applicants: Michelle Khine, Irvine, CA (US); Himanshu Sharma, Sunnyvale, CA (US); Sophia Lin, Rowland Heights, CA (US); Jolie McLane Nokes, Newport Beach, CA (US)

(72) Inventors: Michelle Khine, Irvine, CA (US); Himanshu Sharma, Sunnyvale, CA (US); Sophia Lin, Rowland Heights, CA (US); Jolie McLane Nokes, Newport Beach, CA (US)

(73) Assignee: The Regents of the University of California, Oakland, CA (US)

( * ) Notice: Subject to any disclaimer, the term of this patent is extended or adjusted under 35 U.S.C. 154(b) by 144 days.

(21) Appl. No.: 15/639,406

(22) Filed: Jun. 30, 2017

(65) Prior Publication Data
US 2018/0024030 A1    Jan. 25, 2018

Related U.S. Application Data

(63) Continuation of application No. 13/367,320, filed on Feb. 6, 2012, now abandoned.

(60) Provisional application No. 61/440,350, filed on Feb. 7, 2011.

(51) Int. Cl.
*G01N 1/40* (2006.01)
*G01N 33/545* (2006.01)

(52) U.S. Cl.
CPC ............ *G01N 1/40* (2013.01); *G01N 33/545* (2013.01); *Y10T 436/25375* (2015.01)

(58) Field of Classification Search
CPC .................................................... G01N 1/40
USPC .............................................. 435/6.12; 506/9
See application file for complete search history.

(56) References Cited

U.S. PATENT DOCUMENTS

| | | | | |
|---|---|---|---|---|
| 5,418,136 A | * | 5/1995 | Miller | G01N 33/54373 250/458.1 |
| 6,783,838 B2 | * | 8/2004 | Coleman | B82Y 30/00 428/141 |
| 7,005,259 B1 | * | 2/2006 | McGall | C07H 21/04 422/68.1 |
| 2002/0146745 A1 | * | 10/2002 | Natan | G01N 33/538 435/7.1 |
| 2003/0044781 A1 | * | 3/2003 | Korlach | C12Q 1/6869 435/6.1 |
| 2003/0103878 A1 | * | 6/2003 | Morse | B01J 19/0093 422/198 |
| 2004/0092396 A1 | * | 5/2004 | Glazer | B01J 19/0046 502/439 |
| 2005/0083781 A1 | * | 4/2005 | Caren | B01F 5/061 366/220 |
| 2008/0207466 A1 | * | 8/2008 | Mozdy | C40B 30/10 506/12 |

\* cited by examiner

*Primary Examiner* — Karla A Dines
(74) *Attorney, Agent, or Firm* — Foundation Law Group LLC; JD Harriman

(57) ABSTRACT

Provided are methods of preparing a sample for detection by placing the sample on a shrinkable scaffold and then shrinking the scaffold. An exemplary shrinkable scaffold is a thermoplastic substrate.

15 Claims, 4 Drawing Sheets

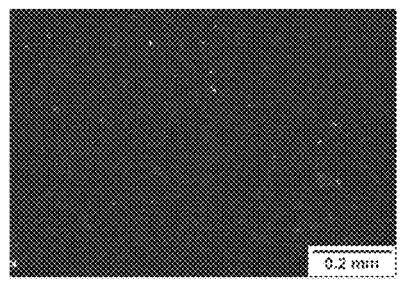 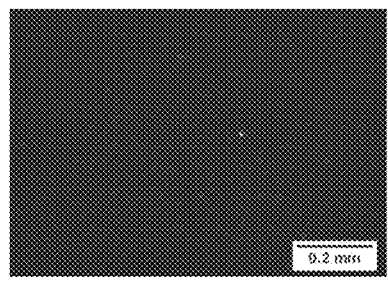 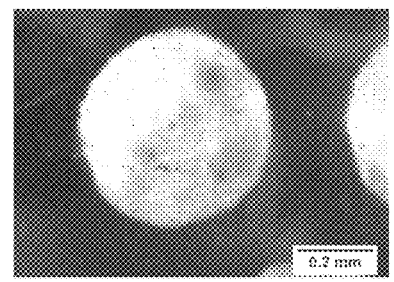
FIG. 5A  FIG. 5B  FIG. 5C
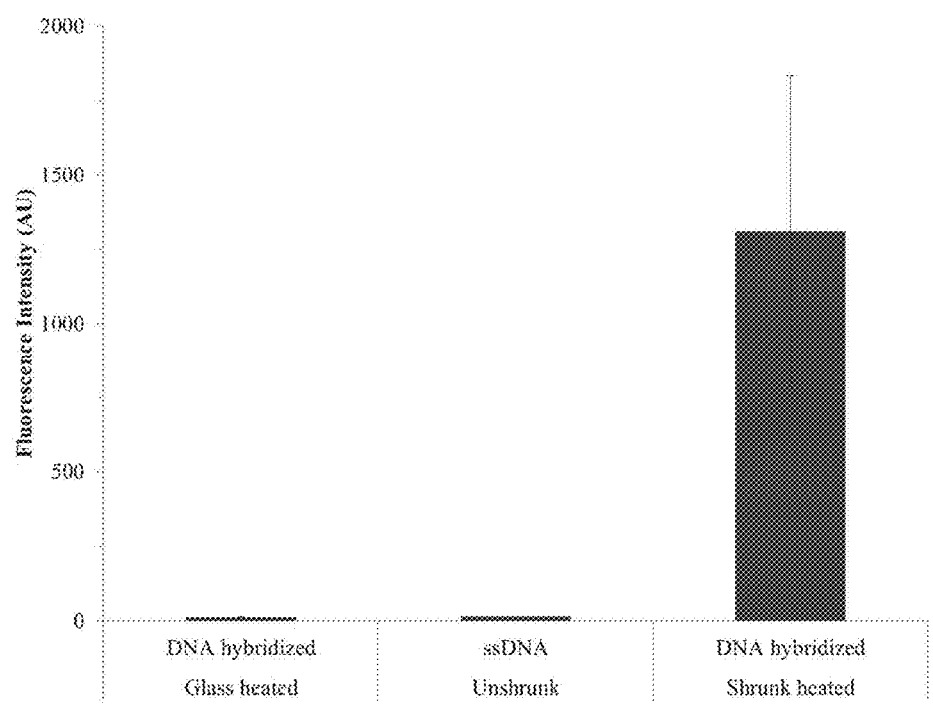
FIG. 6

DETECTION OF LOW CONCENTRATION BIOLOGICAL AGENTS

CROSS-REFERENCE TO RELATED APPLICATIONS

This application is a Continuation of U.S. application Ser. No. 13/367,320, filed Feb. 6, 2012, which claims the benefit under 35 U.S.C. § 119(e) of U.S. Provisional Application No. 61/440,350, filed Feb. 7, 2011, the contents of which are hereby incorporated by reference into the present disclosure.

FIELD OF THE INVENTION

The invention disclosed herein related to the field of detection of biological samples.

BACKGROUND

The amount of a samples available for clinical diagnostics is typically limited or the concentration is low, which makes accurate detection difficult. Therefore, there is unmet market need of methods and devices for assaying samples with high sensitivity.

SUMMARY

The present disclosure provides methods and devices for measuring samples, such as biological samples, especially those at low abundance, with high sensitivity and at low cost. In one embodiment, a sample is disposed on a shrinkable scaffold, and then the shrinkable scaffold is shrunk, reducing the area where the sample is distributed, so as to effectively concentrate the sample on the surface of the scaffold. The increase of concentration can be many fold and lead to greatly increased sensitivity of detection.

It is further contemplated that, in the event that a biological sample, e.g., protein or nucleic acid, is covalently attached to a scaffold having a silica structure, the great increase in signal enhancement is also due to the optical effects stemming from covalent linkage of the biological sample onto the silica structure of the scaffold.

Thus, in one embodiment, the present disclosure provides a method for preparing a sample for detection, comprising shrinking a thermoplastic material comprising a sample disposed on the thermoplastic material, thereby concentrating the sample on the thermoplastic material.

Likewise, another embodiment provides a method for detecting a sample comprising (A) disposing the sample on a thermoplastic material, (B) shrinking the thermoplastic material, and (C) detecting the sample.

In one aspect, the sample comprises a detectable label. In another aspect, the detectable label comprises a fluorescent agent. In yet another aspect, the sample is a biological sample.

In some aspects, detecting comprises measuring the amount of a signal emitted by the sample. If the sample comprises a detectable label, detection can be done by measuring emission of the detectable label. If the sample is not labeled, a detectable label can be added so that it binds to the samples effecting detection of the sample.

The material can be pre-stressed prior to shrinking. When the material is prestressed, the shrinking can be achieved by removing the stress. In another aspect, the shrinking is achieved by heating the material, whether the material has been prestressed.

In some aspects, the shrinking is uniaxial or biaxial. In some aspects, the material is shrunk by at least 60% or more.

Thermoplastic materials suitable for practicing the present technology include, without limitation, a high molecular weight polymer, polyolefin, polyethylene, acrylonitrile butadiene styrene (ABS), acrylic, celluloid, cellulose acetate, ethylene-vinyl acetate (EVA), ethylene vinyl alcohol (EVAL), fluoroplastics (PTFEs, including FEP, PFA, CTFE, ECTFE, ETFE), ionomers kydex, a trademarked acrylic/PVC alloy, liquid crystal polymer (LCP), polyacetal (POM or Acetal), polyacrylates (Acrylic), polyacrylonitrile (PAN or Acrylonitrile), polyamide (PA or Nylon), polyamide-imide (PAI), polyaryletherketone (PAEK or Ketone), polybutadiene (PBD), polybutylene (PB), polybutylene terephthalate (PBT), polyethylene terephthalate (PET), Polycyclohexylene Dimethylene Terephthalate (PCT), polycarbonate (PC), polyhydroxyalkanoates (PHAs), polyketone (PK), polyester polyethylene (PE), polyetheretherketone (PEEK), polyetherimide (PEI), polyethersulfone (PES), polysulfone polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polyvinyl chloride (PVC), polyvinylidene chloride (PVDC) or spectralon. In one aspect, the thermoplastic material comprises polyolefin. In another aspect, the thermoplastic material comprises polyethylene.

Also provided is a substrate having a textured surface prepared by a method of any one of above embodiments.

BRIEF DESCRIPTION OF THE FIGURES

FIG. 2A shows a microscopic picture of a textured surface of the film at the indicated magnification level. FIG. 2B shows a microscopic picture of a textured surface of the film at the indicated magnification level. FIG. 2C shows a microscopic picture of a textured surface of the film at the indicated magnification level. FIG. 2D shows a microscopic picture of a textured surface of the film at the indicated magnification level.

FIG. 5A-FIG. 5C include images showing the fluorescence intensity for (FIG. 5A) DNA hybridized on glass slide (FIG. 5B) single-stranded DNA (non-hybridized) on silica polyolefin (PO) (FIG. 5C) DNA hybridized on silica PO.

FIG. 6 presents a bar chart showing the detection efficiency before (left) and after (right) shrinking as reflected in the images of FIG. 5.

DETAILED DESCRIPTION

Definitions

Figure 1:
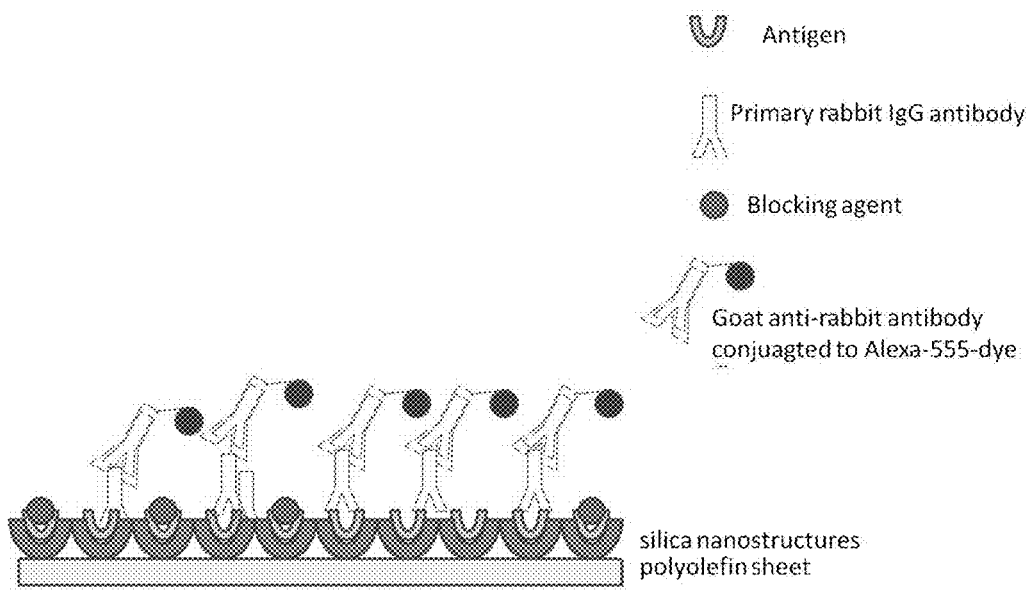
FIG. 1 is a schematic representation of the immunoassay on the silica nanostructures. Bodily fluid such as saliva is deposited on pre-shrunk silica and then incubated with the primary rabbit IgG antibody. The substrate is blocked with BSA before being washed with PBS. Secondary goat anti-rabbit antibody IgG conjugated with Alexa 555 dye is added and left to incubate for 1 hour before being washed again with PBS. The substrate is heat shrunk in an oven before imaged using a fluorescence microscope.
Figure 2A:
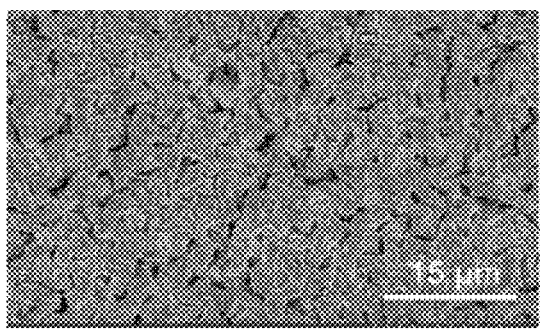
FIG. 2A-FIG. 2D show microscopic pictures of a textured surface of the film at indicated magnification levels.
Figure 2B:
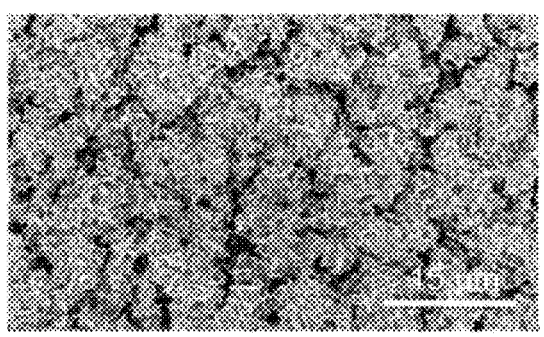
Figure 2C:
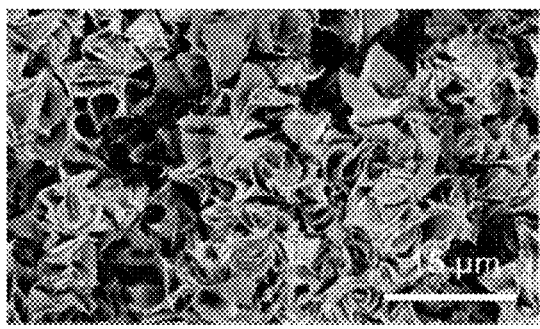
Figure 2D:
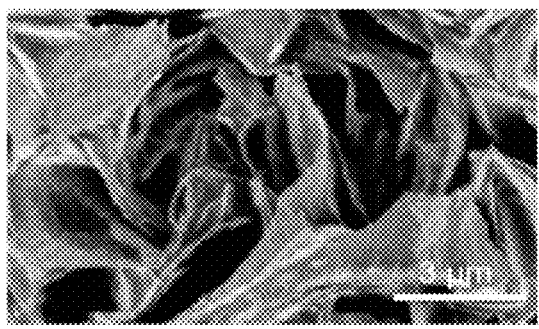

As used herein, certain terms may have the following defined meanings.

As used in the specification and claims, the singular form "a," "an" and "the" include plural references unless the context clearly dictates otherwise.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps for preparing the intended device. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

A "thermoplastic material" is intended to mean a plastic material which shrinks upon heating or upon release of prestress such as a stress created by stretching. In one aspect, the thermoplastic materials are those which shrink uniformly without distortion. The shrinking can be either bi-axially (isotropic) or uni-axial (anisotropic). Suitable thermoplastic materials for inclusion in the methods of this invention include, for example, shape memory polymers, polyolefin, polyethylene, high molecular weight polymers such as acrylonitrile butadiene styrene (ABS), acrylic, celluloid, cellulose acetate, ethylene-vinyl acetate (EVA), ethylene vinyl alcohol (EVAL), fluoroplastics (PTFEs, including FEP, PFA, CTFE, ECTFE, ETFE), ionomers kydex, a trademarked acrylic/PVC alloy, liquid crystal polymer (LCP), polyacetal (POM or Acetal), polyacrylates (Acrylic), polyacrylonitrile (PAN or Acrylonitrile), polyamide (PA or Nylon), polyamide-imide (PAI), polyaryletherketone (PAEK or Ketone), polybutadiene (PBD), polybutylene (PB), polybutylene terephthalate (PBT), polyethylene terephthalate (PET), Polycyclohexylene Dimethylene Terephthalate (PCT), polycarbonate (PC), polyhydroxyalkanoates (PHAs), polyketone (PK), polyester polyethylene (PE), polyetheretherketone (PEEK), polyetherimide (PEI), polyethersulfone (PES), polysulfone polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polyvinyl chloride (PVC), polyvinylidene chloride (PVDC) and spectralon.

In some aspects, the thermoplastic material encompasses polyolefin. A polyolefin is a polymer produced from a simple olefin (also called an alkene) as a monomer. For example, polyethylene is the polyolefin produced by polymerizing the olefin ethylene. Polypropylene is another common polyolefin which is made from the olefin propylene.

In some aspects, the thermoplastic material encompasses shape memory polymers (SMPs). SMPs are polymeric smart materials that have the ability to return from a deformed state (temporary shape) to their original (permanent) shape induced by an external stimulus (trigger), such as temperature change.

Commercially available thermoplastic materials include, without limitation, "Shrinky-Dink" and Solupore®. Shrinky-Dink is a commercial thermoplastic which is used a children's toy. Solupore® is available from Lydall, Inc. of Manchester, Conn.

As used herein, "labels" or "detectable labels" are chemical or biochemical moieties useful for labeling a nucleic acid. "Labels" include fluorescent agents, chemiluminescent agents, chromogenic agents, quenching agents, radionucleotides, enzymes, substrates, cofactors, inhibitors, nanoparticles, magnetic particles, and other moieties known in the art. Labels are capable of generating a measurable signal and may be covalently or noncovalently joined to an oligonucleotide or nucleotide.

In illustrative embodiments, the antibodies may be labeled with a "fluorescent dye" or a "fluorophore." As used herein, a "fluorescent dye" or a "fluorophore" is a chemical group that can be excited by light to emit fluorescence. Some fluorophores may be excited by light to emit phosphorescence. Dyes may include acceptor dyes that are capable of quenching a fluorescent signal from a fluorescent donor dye. Dyes that may be used in the disclosed methods include, but are not limited to, the following dyes and/or dyes sold under the following trade names: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-Hydroxy Tryptamine (HAT); 5-ROX (carboxy-X-rhodamine); 6-Carboxyrhodamine 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV;

BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Cascade Blue™; Cascade Yellow; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3. 1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD—Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant Iavin EBG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

Methods for Preparing a Sample for Analysis

One embodiment of the present disclosure provides a method for preparing a sample for detection, comprising shrinking a thermoplastic material comprising a sample disposed on the thermoplastic material, thereby concentrating the sample on the thermoplastic material.

Likewise, another embodiment provides a method for detecting a sample comprising (A) disposing the sample on a thermoplastic material, (B) shrinking the thermoplastic material, and (C) detecting the sample.

In one aspect, the sample comprises a detectable label. In another aspect, the detectable label comprises a fluorescent agent. In yet another aspect, the sample is a biological sample.

The thermoplastic material can be pre-stressed prior to shrinking. In such a case, the shrinking can be achieved by removing the stress. Such a stress can simply be stretching, either uniaxially or biaxially.

Alternatively, the shrinking can be achieved by heating the material. Depending on the material and desired scale of texture, the temperature can vary. In one aspect, the heating is at least about 200° F., or at least about 250° F., or at least about 275° F., or at least about 300° F., or at least about 350° F.

In some aspects, the material is treated with a plasma before the shrinking. It has been demonstrated that plasma treatment of a thermoplastic material, such as a polyethylene (PE) film, creates a stiff layer at the surface of a relatively softer bulk PE. Leveraging the inherent retraction properties of the thermoplastic material at elevated temperature, the mismatch in stiffness between two layers will cause the stiff outer layer to buckle and form controllable textures or wrinkles.

Plasmas can be prepared with methods known in the art and can vary depending on availability of sources. In one embodiment, the plasma is oxygen plasma, helium plasma, or hydrogen plasma. In a particular embodiment, the plasma is oxygen plasma.

The duration of plasma treatment can vary and depend on the desired scale of the texture and/or the thermoplastic material, for instance. In one aspect, the plasma treatment takes more than about 10 seconds, or alternatively more than about 20 seconds, about 30 seconds, about 1 minute, about 2 minutes, about 3 minutes, about 4 minutes, about 5 minutes, about 7 minutes, about 10 minutes, about 15 minutes, about 20 minutes, about 25 minutes, or about 30 minutes. In another aspect, the plasma treatment takes less than about 60 minutes, or alternatively less than about 45 minutes, about 30 minutes, about 25 minutes, about 20 minutes, about 15 minutes, about 10 minutes, about 7 minutes, about 5 minutes, about 4 minutes, about 3 minutes, about 2 minutes, about 1 minute, about 30 seconds, or about 20 seconds. In some aspects, the treatment is carried out in a closed chamber. In some aspects, the treatment is carried out in a handheld corona discharger.

The thermoplastic material can be pre-stressed prior to the plasma treatment. In such a case, the shrinking can be achieved by removing the stress. Such a stress can simply be stretching, either uniaxially or biaxially.

Shrinking of the material can be uniaxial or biaxial. When the material is shrunk uniaxially, the texture may be one dimensional. When the material is shrunk biaxially, the texture may be two dimensional.

In some embodiments, the material is shrunk, uniaxially or biaxially, by at least about 60%, or alternatively at least about 70%, about 75%, about 80%, about 85%, about 90%, about 91%, about 92%, about 93%, about 94%, about 95%, about 96%, about 97%, about 98%, or about 99% from its original size.

Still, in some aspects, the material is etched, prior to deposition of the sample, to provide room for holding the sample. Such etching, in one embodiment, also contributes to the enhanced signal detection. Methods of etching and related shrinking are provided in WO 2009/064816, the content of which is incorporated into the present disclosure in its entirety, by reference.

In one aspect, the sample is attached to the material. The attachment can be covalent or non-covalent. In one aspect, the attaching is covalent. In a particular aspect, the covalent attachment involves a linker, such as but not limited to, biotin and Poly (L-glutamic acid) (Pglu). In one aspect, the sample is a biological sample, including but not limited to protein, nucleic acids, such as DNA and RNA.

In some embodiments, the material is shrunk, uniaxially or biaxially, by at least about 60%, or alternatively at least about 70%, about 75%, about 80%, about 85%, about 90%, about 91%, about 92%, about 93%, about 94%, about 95%, about 96%, about 97%, about 98%, or about 99% from its original size.

In some embodiments, the concentration of the sample is increased by at least about 5 fold, or alternatively about 5, or about 6, or about 7, or about 8, or about 9, or about 10, or about 12, or about 14, or about 16, or about 18, or about 20, or about 25, or about 30, or about 40, or about 50, or about 60, or about 70, or about 80, or about 90, or about 100 or about 200 fold.

Further, some embodiments of the present disclosure provide samples prepared by any of the disclosed methods.

EXPERIMENTAL EXAMPLES

Example 1

This example illustrates preparation of an antibody for fluoroimmunoassay. A thin layer of silica is deposited on a heat shrink film, polyolefin, by an E-beam evaporation process. Biological molecules, in this case rabbit immunoglobin (IgG) is microcontact printed on the solid substrate and then blocked with blocking solution for 2 hours at room temperature. After 2 hours, the blocking solution is washed and then the goat anti-rabbit conjugated to AlexaFluor 555 is added and after 2 hr incubation the fluorescence signal is measured. After measuring the fluorescence signal, the sample is shrunk in an oven by heating sequentially to 115° C. for 30 minutes, 135° C. for 10 minutes, and 155° C. The inherent ability of the polyolefin polymer to shrink helps with increasing the concentration of the protein and increasing the fluorescent signal enhancement by 16 fold. The experimental procedure is illustrated in FIG. 1. FIG. 2A-D show the nanostructure of the shrunk surface of the film.

Bodily fluids such as saliva which have antigens that can be recognized by the primary antibody can also be assayed the same way.

Example 2

This example demonstrates that amplification in sample signal can be achieved by shrinking the thermoplastic surface. The amplification utilizes a protein's ability to naturally adsorb onto a surface and the subsequent increase in detection signal is attributed to concentrating the sample on the thermoplastic material and increasing the surface area. Further, the method illustrated here involves chemically functionalizing the thermoplastic material for covalent attachment of biological samples.

Figure 3A:
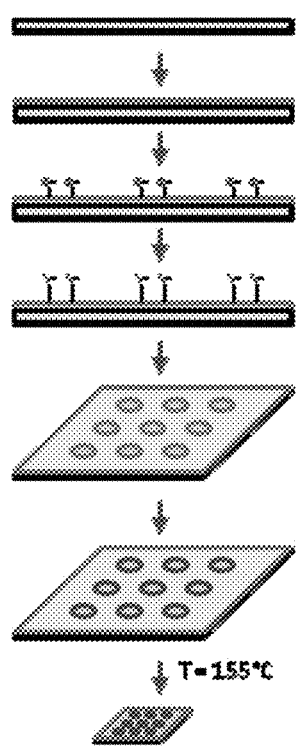
FIG. 3A illustrates the process of shrinking a surface carrying a biological sample.

Modification of the clean thermoplastic surface starts with depositing a thin layer of silica onto the surface by ion beam sputter coater, followed by oxygen plasma treatment for the introduction of hydroxyl groups. The surface is then aminated by submerging into a 5% (v/v) (3-aminopropyl) trimethoxysilane (APTMS) ethanolic solution for 2 hours at room temperature. The thermoplastic substrate is then washed with 100% ethanol and ddH$_2$O, and allowed to cure overnight at room temperature. The aminated thermoplastic surface is reacted with NHS-ester activated biotin (1 mg/ml) for 2 hrs, washed twice with 1× PBS and ddh$_2$O, and then incubated with 1 μL volumes of streptavidin-TRITC for 2 hrs (10 μg/ml). Fluorescent signal is measured. The thermoplastic substrates are shrunk by heating to T=160° C. and fluorescent signal is measured again. This procedure is illustrated in FIG. 3a.

Figure 3B:
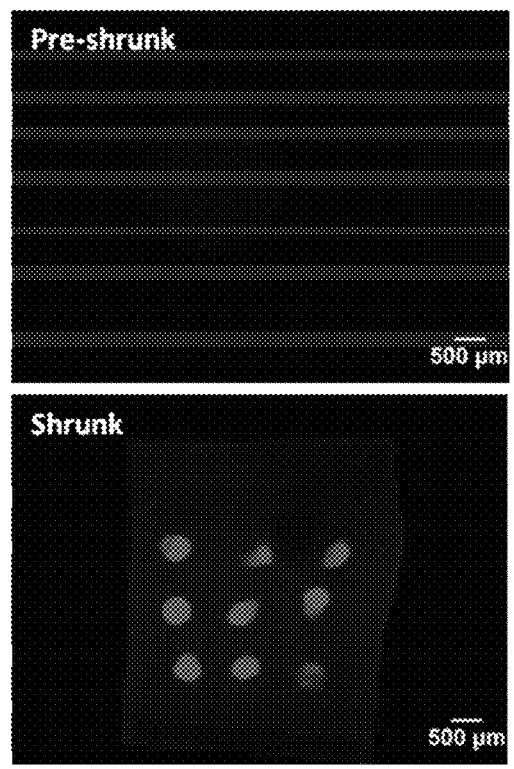
FIG. 3B includes images showing the detected signal before (upper) and after (lower) shrinking.
Figure 4:
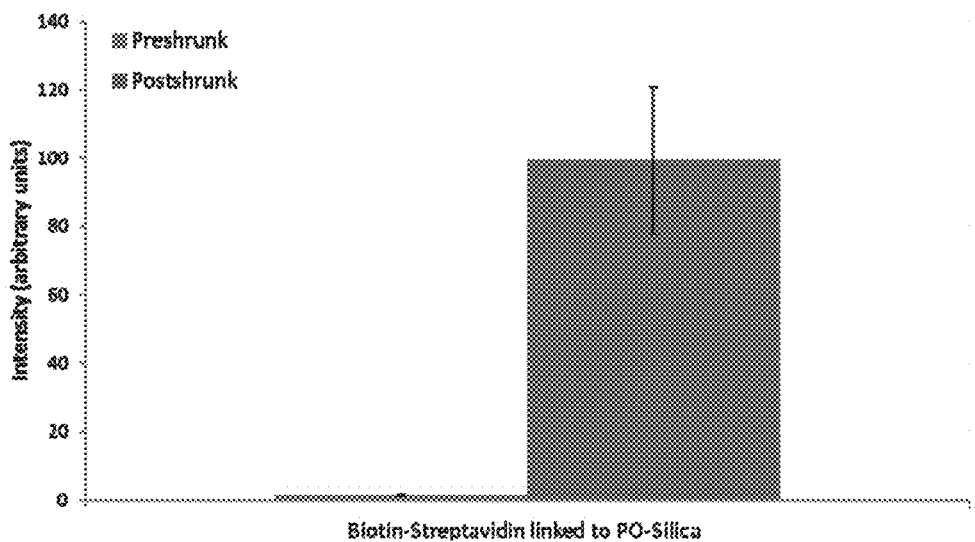
FIG. 4 presents a bar chart showing the detection efficiency before (left) and after (right) shrinking.

The observed fluorescent signal of the shrunk thermoplastic substrates demonstrates signal enhancement ranging between 55 to 75 fold (see actual images in FIG. 3b and comparison charts in FIG. 4).

Example 3

This is another example demonstrating that amplification in sample signal can be achieved by shrinking the thermoplastic surface.

This procedure involves fabricating a DNA microarray by laser etching a microwell pattern in polyolefin (PO) sealing tape and adhering to a polystyrene (PS) or PO thermoplastic. Features are etched into the exposed thermoplastic surface and silica is sputtered on top. Isopropyl alcohol (IPA) is used to remove the PO sealing tape without disturbing the silica. The exposed silica-coated wells are treated with oxygen plasma to introduce hydroxyl groups and then chemically modified with 5% (v/v) (3-aminopropyl)trimethoxysilane (APTMS) ethanolic solution for 4 hours at room temperature. Poly (L-glutamic acid) (Pglu) is then reacted with the aminated thermoplastic surface in the presence of 1-Ethyl-3-(3-dimethylaminopropyl)carbodiimide (EDC)/N-Hydroxysuccinimide (NHS). Single stranded DNA is flowed over the substrate to bind to the Pglu through the formation of amide bonds. The thermoplastic substrate is shrunk by heating to T=160° C. Complementary stranded DNA tagged with Cy3 is flowed over the shrunk substrate and fluorescent signal is measured (FIG. 5).

The observed fluorescent signal of biological sample shows a signal enhancement of around 90 fold (FIGS. 5 and 6).

While the present invention is exemplified and illustrated by the use of polystyrene sheets to fabricate channel structures and molds, it would be obvious to those of skill in the art that any thermoplastic receptive material that can be patterned to control the dimensions of the channel defining walls and thereby their size, can be used to fabricate the devices disclosed and claimed herein. In addition, although several other embodiments of the invention are described herein in detail, it will be understood by those skilled in the art that variations may be made thereto without departing from the spirit of the invention or the scope of the appended claims.

The invention claimed is:

1. A method for preparing a sample for detection of a fluorescently labeled polynucleotide suspected to be present in the sample by detecting the amount of fluorescence emitted by the fluorescently labeled polynucleotide, comprising:
   laser etching a microwell pattern in a polyolefin (PO) sealing tape and adhering the tape to a surface of a thermoplastic material;
   etching features into the surface of the thermoplastic material;
   applying a silica surface to the surface of the thermoplastic material:
   removing the sealing tape from the surface of the thermoplastic material;
   treating the silica surface with plasma;
   covalently attaching the polynucleotide on the silica surface of the thermoplastic material;
   heating and shrinking the thermoplastic material thereby concentrating the sample on the silica surface and to provide a rough porous substrate that results in an optical effect of light scattering.

2. The method of claim 1, wherein the material is prestressed prior to the shrinking and the shrinking comprises removing the stress.

3. The method of claim 1, wherein the shrinking is uniaxial or biaxial.

4. The method of claim 1, wherein the material is shrunk by at least 60%.

5. The method of claim 1, wherein the thermoplastic material comprises a high molecular weight polymer, polyolefin, a shape memory polymer, polyethylene, acrylonitrile butadiene styrene (ABS), acrylic, celluloid, cellulose acetate, ethylene-vinyl acetate (EVA), ethylene vinyl alcohol (EVAL), fluoroplastics (PTFEs, including FEP, PFA, CTFE, ECTFE, ETFE), ionomers kydex, a trademarked acrylic/PVC alloy, liquid crystal polymer (LCP), polyacetal (POM or Acetal), polyacrylates (Acrylic), polyacrylonitrile (PAN or Acrylonitrile), polyamide (PA or Nylon), polyamide-imide (PAI), polyaryletherketone (PAEK or Ketone), polybutadiene (PBD), polybutylene (PB), polybutylene terephthalate (PBT), polyethylene terephthalate (PET), Polycyclohexylene Dimethylene Terephthalate (PCT), polycarbonate (PC), polyhydroxyalkanoates (PHAs), polyketone (PK), polyester polyethylene (PE), polyetheretherketone (PEEK), polyetherimide (PEI), polyethersulfone (PES), polysulfone polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polyvinyl chloride (PVC), polyvinylidene chloride (PVDC) or spectralon.

6. The method of claim 5, wherein the thermoplastic material comprises polyolefin.

7. The method of claim 5, wherein the thermoplastic material comprises polyethylene.

8. The method of claim 1, wherein the sample comprises a biological sample.

9. The method of claim 8 wherein the biological sample is microcontact printed on the material.

10. The method of claim 1, wherein the plasma is oxygen plasma.

11. The method of claim 1, wherein the material is etched before the sample is deposited on the material.

12. The method of claim 11 wherein the material is etched by laser etching.

13. A sample prepared by a method of claim 1.

14. The method of claim 1 further comprising detecting any polynucleotide if present in the sample by detecting the fluorescence emitted by the label.

15. The method of claim 1 wherein applying the silica surface to the surface of the thermoplastic material comprises e-beam vaporization or sputtering prior to covalently attaching the polynucleotide on the silica surface.

* * * * *